United States Patent
Hu et al.

(10) Patent No.: US 10,420,737 B2
(45) Date of Patent: Sep. 24, 2019

(54) HEPATOTOXICITY-FREE PHARMACEUTICAL COMPOSITION CONTAINING ACETAMINOPHEN DRUGS

(71) Applicant: NATIONAL DEFENSE EDUCATION AND RESEARCH FOUNDATION, Taipei (TW)

(72) Inventors: Oliver Yao-Pu Hu, Taipei (TW); Tung-Yuan Shih, Taipei (TW)

(73) Assignee: NATIONAL DEFENSE EDUCATION AND RESEARCH FOUNDATION, Taipei (TW)

( * ) Notice: Subject to any disclaimer, the term of this patent is extended or adjusted under 35 U.S.C. 154(b) by 0 days.

(21) Appl. No.: 14/441,317

(22) PCT Filed: Nov. 13, 2013

(86) PCT No.: PCT/CN2013/087049
§ 371 (c)(1),
(2) Date: Oct. 21, 2016

(87) PCT Pub. No.: WO2015/070396
PCT Pub. Date: May 21, 2015

(65) Prior Publication Data
US 2017/0172950 A1   Jun. 22, 2017

(51) Int. Cl.
| | | |
|---|---|---|
| *A61K 47/02* | (2006.01) | |
| *A61K 47/10* | (2017.01) | |
| *A61K 47/12* | (2006.01) | |
| *A61K 47/14* | (2017.01) | |
| *A61K 47/22* | (2006.01) | |
| *A61K 47/26* | (2006.01) | |
| *A61K 47/32* | (2006.01) | |
| *A61K 47/36* | (2006.01) | |
| *A61K 47/38* | (2006.01) | |
| *A61K 47/46* | (2006.01) | |
| *A61K 31/167* | (2006.01) | |
| *A61K 31/765* | (2006.01) | |

(52) U.S. Cl.
CPC .......... *A61K 31/167* (2013.01); *A61K 31/765* (2013.01); *A61K 47/14* (2013.01); *A61K 47/46* (2013.01); *A61K 47/02* (2013.01); *A61K 47/10* (2013.01); *A61K 47/12* (2013.01); *A61K 47/22* (2013.01); *A61K 47/26* (2013.01); *A61K 47/32* (2013.01); *A61K 47/36* (2013.01); *A61K 47/38* (2013.01)

(58) Field of Classification Search
CPC .............. A61K 2300/00; A61K 31/167; A61K 31/765; A61K 47/02; A61K 47/10; A61K 47/12; A61K 47/14; A61K 47/22; A61K 47/26; A61K 47/32; A61K 47/36; A61K 47/38; A61K 47/46
See application file for complete search history.

(56) References Cited

FOREIGN PATENT DOCUMENTS

WO    WO 2007/050631 A2 *   5/2007

\* cited by examiner

*Primary Examiner* — Kara R McMillian
(74) *Attorney, Agent, or Firm* — Birch, Stewart, Kolasch & Birch, LLP

(57) ABSTRACT

A new compound composition that is free of a side effect to a liver and used for alleviating the toxicity of an acetaminophen (APAP) medicament to the liver. The compound composition comprises (a) a pharmaceutically effective amount of acetaminophen and (b) a frequently-used safe and pharmaceutically acceptable excipient that can be combined with one or more than two medicaments that can reduce the toxicity of a drug via liver enzyme CYP2E1 metabolism to the liver. The compound is selected from the following group: Tween 20, microcrystalline cellulose, dicalcium phosphate, polyoxyethylene 23 lauryl ether, saccharin, mannitol, polyoxyethylene alkyl ether, sucralose, pyrrolidone, sodium starch glycolate, acrylic resin S100, carboxymethyl cellulose sodium, polyoxyethylene polyoxypropylene, menthol, low-substituted hydrocarbon propyl cellulose, pregelatinized starch, Dextrates NF hydrated, citric acid, polyoxyethylene castor oil, colloidal silica, polyethylene glycol monostearate aliphatic ester, sorbic acid, lemon oil, hydroxypropyl cellulose, sorbitol, acesulfame potassium, hypromellose phthalate, lactose monohydrate, maltodextrin, Brij 58, Brij 76, Tween 80, Tween 40, PEG 400, PEG 4000, PEG 2000, and the like, so as to reduce the side effect of the toxicity caused by acetaminophen to the liver.

4 Claims, 2 Drawing Sheets

HEPATOTOXICITY-FREE PHARMACEUTICAL COMPOSITION CONTAINING ACETAMINOPHEN DRUGS

BACKGROUND OF THE INVENTION

1. Field of the Invention

The present invention relates to a new hepatotoxicity-free pharmaceutical composition containing acetaminophen (APAP), in particular, a new pharmaceutical composition that contains a combination of acetaminophen and one or any combinations of common and pharmaceutically acceptable excipients that can inhibit the activity of P450 2E1 (CYP2E1) to reduce hepatotoxicity induced by acetaminophen.

2. Description of the Prior Art

Acetaminophen (also known as Panadol) is also called paracetamol or N-acetyl-para-aminophenol (APAP) and is the most widely used pain-relieving and fever-reducing drug on the market. Each year, numerous cases of drug intoxication or suicide are reported due to improper use of APAP, and liver damage caused by APAP is the main cause of severe diseases and death. A number of clinical studies have demonstrated that hepatotoxicity induced by APAP is preventable and early diagnosis along with real-time administration of the antidote N-acetylcysteine (NAC) can effectively prevent the occurrence of hepatotoxicity.

Early detection of acetaminophen overdose is necessary because the best prognosis can be achieved if the antidote is given within 8 hours after poisoning. The early signs of drug intoxication include discomfort, nausea and vomiting. However, some patients may show no signs of intoxication at the early stage (stage 1) even if their blood concentrations of acetaminophen are at the poisoning levels and their abnormal liver function is apparently abnormal. The signs of hepatotoxicity, such as abdominal pain, persistent vomiting, jaundice, right upper quadrant pain, usually become apparent 24-48 hours after ingestion of a significant amount of acetaminophen (stage 2). Serum amintransferase usually starts to rise 16 hours after administration with clinical symptoms. Stage 3 usually occurs 3-4 days after administration and the degree of liver damage as well as prognosis can be well predicted at the time. The signs of hepatotoxicity progress from mild symptoms with elevated liver function values (AST>1,000 IU/L) to severe acute fulminant hepatitis accompanied by metabolic acidosis, jaundice, hyperglycemia, AST>1,000 IU/L, abnormal blood clotting and hepatic/brain lesions. Stage 4 will cause oliguria renal failure or death in severe cases.

Some patients with acetaminophen intoxication show only mild liver damage but with severe renal toxicity which is mainly caused by direct metabolism of APAP in P-450s (cytochrome P450s, CYPs) of the renal tubule. Nonetheless, acute renal failure may also result from hepatorenal syndrome caused by acute liver failure and the fraction excretion of Na (FeNa) can be used for differentiation primary renal damage (FeNa>1) from hepatorenal syndrome (FeNa>1). The calculation formula for FeNa is (Sodiumurinary÷Creatinineurinary)÷(Sodiumplasma÷Creatinineplasma)×100.

The peak concentration of acetaminophen in blood is achieved 1-2 hours after oral administration and a significant amount is eliminated by liver, more than 90% is conjugated to glucuronide and sulfate and form non-toxic metabolites and only less than 5% is eliminated by different CYPs, including CYP2E1, CYP1A2 and CYP3A4, and among which CYP2E1 and CYP1A2 are the major enzymes for metabolism. The metabolite produced by these enzymes, N-acetyl-p-benzoquinoneimine (NAPQI, as shown in FIG. 1) is a very active electrophile. Under normal conditions, NAPQI will react immediately with glutathione in the cell and form non-toxic mercaptide. Overdose of acetaminophen makes the consumption rate of glutathione greater than its synthesis rate and when the glutathione level of the cell is lower than the normal range of 30%, NAPQI will bind to large molecules or nucleic acids containing cysteine and lead to liver damage. From histochemical stains, NAPQI will bind to the thiol group of cysteine and form a covalent bond in centrilobular areas before occurrence of liver cell necrosis.

Patients with liver disease, alcohol addiction or who are taking drugs which may induce the activity of P450 such as Carbamazepine, Ethanol, Isoniazid, Phenobarbital (may be other barbiturates), Phenytoin, Sulfinpyrazone, Sulfonylureas, Rifampin and Primidone are the susceptible groups of developing severe hepatotoxicity caused by APAP and may easily die if the patient also develops complications such as adult respiratory distress syndrome, cerebral edema, uncontrollable bleeding, infection or Multiple organ dysfunction syndrome (MODS). Take alcohol for example, alcohol is mainly eliminated by CYP2E1 of liver and its mechanism of APAP intoxication is divided into three stages: at the first stage alcohol competes the receptors for CYP2E1 with APAP in the liver and the concentration of NAPQI will reduce during the stage, at the second stage alcohol prolongs the half life of CYP2E1 from 7 hours to 37 hours which increases the level of CYP2E1 in the liver and the concentration of NAPQ1 will is slowly increase during this stage, and at the third stage, during alcohol withdrawal, more CYP2E1 is found in the liver to eliminate acetaminophen and consequently the toxic metabolites of acetaminophen increases significantly and lead to liver damage. Recent studies have shown that diallyl sulfide can effectively prevent hepatotoxicity caused by acetaminophen in mice and further demonstrated diallyl sulfide can inhibit the activity of CYP2E1. It is speculated that the protection mechanism of diallyl sulfide against hepatotoxicity induced by acetaminophen is by inhibition of the production of the intermediate NAPQI from acetaminophen.

Use of invasive and non-invasive methods to investigate the liver function of rats so as to monitor progress of liver damage and screen for liver diseases. The most common methods used include measurement of the levels of aspartate aminotransferase (AST), alanine aminotransferase (ALT) and alkaline phosphatase, liver cell products such as bilirubin and albumin as well as coagulation factors by prothrombin time prior to testing. Quantitative liver function is measured based on the serum concentrations of the substrates that almost exclusively processed in the liver. Elimination of these substrates is determined according to the blood flow of the hepatic portal vein and artery and the effects of liver cells on these substrates. Liver blood flow is associated with the levels of the substrates of liver; on the contrary, elimination of the substrate depends on the metabolic capacity in liver.

Galactose is a saccharine that has a high extraction ratio and 90% is eliminated by liver. In liver, galactose is converted into glucose-1-phosphate by galactokinase through a process called epimerization. The reaction of galactokinase is the rate-limiting step of galactose metabolism in liver cells. The high extraction rate of galactose makes metabolism of galactose which depends on liver blood flow and liver function the most important method for assessing liver function. At present, no definite rules are available for assessing residual liver function of rats. Measurement of the metabolic capacity of a definite compound (e.g. galactose) can help prediction of the rate-limiting step of a certain metabolic pathway and provide the representative values of residual liver function.

The inventor of present invention examined the patients with chronic hepatitis, cirrhosis and liver cancer by using galactase single point (GSP) and the result indicates GSP can accurately identify these liver diseases. GSP has been successfully applied to measurement of elimination in patients with liver disease, for example, the residual liver function of promazine and cefoperazone. In addition, GSP has become one of the methods for testing liver function recommended by the U.S. FDA in the Guidance for Industry.

In summary, a number of defects remain in the uses of acetaminophen.

SUMMARY OF THE INVENTION

The inventor of the present invention developed a new hepatotoxicity-free pharmaceutical composition containing acetaminophen (APAP) to overcome the hepatotoxicity caused by traditional use of acetaminophen.

In one aspect, the invention provides a new hepatotoxicity-free pharmaceutical composition containing acetaminophen (APAP) drugs, comprising of (a) a pharmaceutically effective dose of acetaminophen and (b) one or two compounds that can reduce hepatotoxicity produced by metabolism of CYP2E1 in liver.

According to the invention, the compound is selected from at least one of the following compounds or its combinations thereof: polyethylene glycol sorbitan monolaurate, Tween 20, Microcrystalline cellulose, dicalcium phosphate dihydrate, Brij 35, saccharin, mannitol, cremophor RH40, sucralose, crospovidone, sodium starch glycolate, eudragit S100, croscarmellose sodium, pluronic F68, menthol, low-substituted hydroxypropyl cellulos, pregelatinized starch, dextrates NF hydrated, citric acid, cremophor EL, aerosil 200, myrj 52, sorbic acid, lemon oil, hydroxypropyl cellulose, sorbitol, acesulfame potassium, hydroxypropyl methylcellulose, lactose monohydrate, maltodextrin, Brij 58, Brij 76, Tween 80, Tween 40, PEG 400, PEG 4000, PEG 8000, Span 60, sodium benzoate, hydroxy ethylmethylcellulose, methylcellulose, Span 80, sodium cyclamate, glyceryl behenate, oxide red, glycerin monostearate, copovidone K28, starch acetate, magnesium stearate, sodium lauryl sulfate, providone K30 and PEG 2000.

According to the invention, the compound is selected from at least one of the is following groups or its combinations thereof and its effective dose is specified: the amount of polyethylene glycol sorbitan monolaurate (Tween 20) is 0.17-5.5 g, the amount of microcrystalline cellulose is 100-1000 mg, the amount of dicalcium phosphate dihydrate is 10-250 mg, the amount of Brij 35 is 100-1000 mg, the amount of saccharin is 10-40 mg, the amount of mannitol is 10-250 mg, the amount of cremophor RH40 is 0.17-5.5 g, the amount of sucralose is 10-250 mg, the amount of crospovidone is 0.17-5.5 g, the amount of sodium starch glycolate is 0.17-5.5 g, the amount of sudragit S100 is 0.17-5.5 g, the amount of croscarmellose sodium is 0.17-5.5 g, the amount of pluronic F68 is 1.4-5.5 g, the amount of menthol is 8-34 mg, the amount of low-substituted hydroxypropyl cellulos is 0.19-0.82 g, the amount of pregelatinized starch is 1.7-5.5 g, the amount of dextrates NF hydrated is 0.17-5.5 g, the amount of citric acid is 10-42 mg, the amount of cremophor EL is 1.7-5.5 g, the amount of aerosil 200 is 0.17-5.5 g, the amount of myrj 52 is 1.4-5.5 g, the amount of sorbic acid is 6-24 mg, the amount of lemon oil is 0.17-5.5 g, the amount of hydroxypropyl cellulose is 0.17-5.5 g, the amount of sorbitol is 0.17-5.5 g, the amount of acesulfame potassium is 1.4-5.5 g, the amount of hydroxypropyl methylcellulose is 0.17-5.55 g, the amount of lactose monohydrate is 6-24 mg, the amount of maltodextrin is 0.17-5.55 g, the amount of Brij 58 is 0.17-5.5 g, the amount of Brij 76 is 0.17-5.5 g, the amount of Tween 80 is 0.17-5.5 g, the amount of Tween 40 is 1.4-5.5 g, the amount of PEG 400 is 1.4-5.5 g, the amount of PEG 4000 is 1.4-5.5 g, the amount of PEG 8000 is 1.4-5.5 g, the amount of Span 60 is 1.4-5.5 g, the amount of sodium benzoate is 2.9-11.9 mg, the amount of hydroxy ethylmethylcellulose is 0.17-5.5 g, the amount of methylcellulose is 0.17-5.5 g, the amount of Span 80 is 1.4-5.5 g, the amount of sodium cyclamate is 3.3-13.2 mg, the amount of glyceryl behenate is 17.4-69.9 mg, the amount of oxide red is 11.3-45.2 mg, the amount of glycerin monostearate is 1.4-5.5 g, the amount of copovidone K28 is 0.17-5.5 g, the amount of starch acetate is 0.17-5.5 g, the amount of magnesium stearate is 9.7-39.0 mg, the amount of sodium lauryl sulfate is 4.7-19.0 mg, the amount of Providone K30 is 0.18-0.73 mg, and the amount of PEG 2000 is 1.4-5.5 g.

According to the invention, the best composition of the compound is selected from the combination of mannitol and sucralose.

According to the invention, the compound is used separately, simultaneously, or sequentially.

According to the invention, hepatotoxicity produced by acetaminophen and/or the CYP2E1 metabolite in liver is reduced by administration of the compound in the form of gel, spray, pastilles, torches, or dispersible tablets.

According to the invention, the compound is included in the medicine pack, kit or patient pack.

In another aspect, the invention provides a use of the hepatotoxicity-free pharmaceutical formulation containing acetaminophen drugs manufactured for treatment.

DETAILED DESCRIPTION OF THE PREFERRED EMBODIMENT

Figure 1:
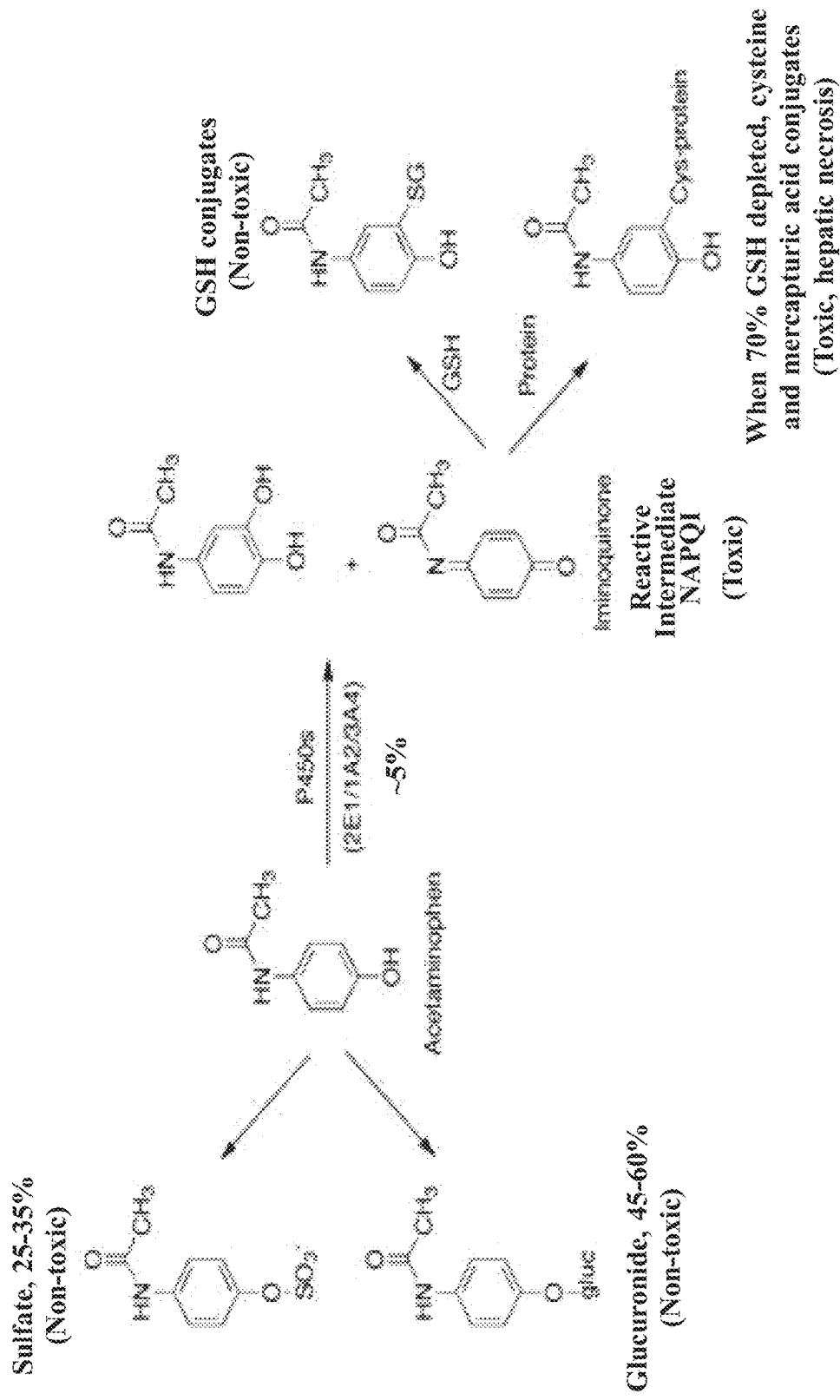
FIG. 1 shows the metabolic pathway of acetaminophen (APAP) in liver.

The present invention is further illustrated by the following examples, which are provided for the purpose of demonstration rather than limitation.

In view of the aforesaid disadvantages of side effects such as hepatotoxicity is caused by the above-mentioned conventional uses of acetaminophen, the inventor of the present invention desirably wants to improve and innovate, and after many years of research, has finally succeeded in researching and developing the new acetaminophenol having no side effects to the liver.

According to the invention, the new acetaminophen pharmaceutical composition induced hepatotoxicity in rats and this is used as an animal model to investigate the effect of hepatotoxicity caused by acetaminophen in rats by combining acetaminophen with one or any combination of CYP2E1 inhibitors. In addition to the use of common markers of hepatotoxicity and histological tissue sections, GSP is also used to quantify residual liver function of the rats for further assessment.

Unless defined otherwise, all technical and scientific terms used herein have the meaning commonly understood by a person skilled in the art to which this invention belongs.

In the invention, when used in two or more compounds and/or pharmaceutical formulations, the term "combination" refers to the materials that containing said two or more compounds and/or pharmaceutical formulations. As used herein, the term "combined" and "combining" used in the invention have the meanings ascribed to them unless specified otherwise.

Pharmaceutical kits, pharmaceutical packs or patient packs, wherein two or more compounds/pharmaceutical formulations are co-packed or co-present (if the compound(s) is packaged as the dosage unit in a batch).

Present invention will be better elucidated when read in conjunction with the following examples; however, it should be understood that the invention is not limited to the preferred embodiments shown. Unless otherwise specified, all materials used herein are commercially available materials and can be easily acquired.

EXAMPLE 1

Animal studies of combination use of acetaminophen and one pharmaceutically acceptable excipient or its combinations thereof to reduce hepatotoxicity induced by drugs.

Materials and Methods

1. Materials

All organic solvents are HPLC grade and are purchased from Tedia (Fairfield, Ohio, USA). APAP is purchased from Sigma (St. Louis, Mo. USA), galactose injectable solution is manufactured by Southern Photochemical Co. and is prepared by dissolving 400 g of galactose (Sigma) in 1 L of buffer solution containing isotonic salts for injections.

2. Animals

Male SD (Sprague-Dawley) rats weighing 175-280 g were purchased from the National Laboratory Animal Center (NLAC), Taiwan. The study was conducted in accordance with the Guidelines for Conducting Animal Studies of the National Health Research Institute and all rats were placed in the air/humidity controlled environment under the 12 hours of day/12 hours of night cycle and with unlimited water and food supply. During the course of the study, the weights of rats were monitored continuously with normal water supply.

3. Treatments

In vitro selection of effective CYP2E1 inhibitors and conduct animal studies to examine APAP-induced hepatotoxicity by combination use or no combination use of APAP. For hepatotoxicity test, rats were fed with a single dose of APAP in the amount of 1000 mg per kilogram of body weight to induce hepatotoxicity. Rats in the liver protection groups were fed with 1.67 mg of dicalcium phosphate per kilogram of body weight, or 1.67 mg of mannitol per kilogram of body weight, or 1.67 mg of menthol per kilogram of body weight, or 1.67 mg of HUEXC041 per kilogram of body weight, or 1.67 mg of mannitol and 1.67 mg of sucralose per kilogram of body weight, or 0.83 mg of mannitol and 0.83 mg of sucralose per kilogram of body weight, or 0.42 mg of mannitol and 0.42 mg of sucralose per kilogram of body weight, or 0.17 mg of mannitol and 0.17 mg of sucralose per kilogram of body weight, and combined with oral administration of a single dose of 1000 mg APAP per kilogram of body weight through tube feeding. Measurements of the serum aspartate aminotransferase (AST) and alanine aminotransferase (ALT) are used as indicators of liver inflammation. GSP was performed 16 hours before and after administration of the drugs to analyze the residual liver function of rats. Meanwhile, pathological changes of each test group were analyzed using histological tissue sections to assess the mechanism(s) of liver damage or liver protection.

4. Blood Samples

After completion of the treatments, rats were sacrificed under ether anesthesia, and blood was collected from the tail artery of the rats and placed in a test tube containing EDTA. The plasma was centrifuged at 13,000 at 4° C. for 15 minutes and the isolated plasma was transferred to Eppendorf tubes in aliquots and stored at −80° C.

5. Biochemical Analysis

Liver damage is quantified by measuring plasma AST and ALT activity. AST and ALT are common indicators of hepatotoxicity and are measured by using the Synchron LXi 725 system (Beckman Instruments, U.S.).

6. Optic Microscope

Following scarification of the rats, histological analysis was performed. Liver samples were fixed with 10% phosphate-buffered formalin, dehydrated an embedded in paraffin, Sections were prepared in 5 μm thickness and then stained with hematoxylin and eosin and subjected to Periodic acid Schiff stain (PAS). The stained sections were observed under the optic microscope.

7. Quantitative Tests of Liver Function

After the study was completed, all rats were subjected to GSP test. Rats were i.v. injected with 0.4 g/ml BW galactose solution 0.5 g/kg within 30 seconds and one blood sample was collected at 5, 10, 15, 30, 45 and 60 minutes post injection from the tail vein. Colorimetric galactose dehydrogenase is used to quantify the concentration of galactose and the test concentration ranges from 50 to 1,000 μg/ml. The within-day variation of each concentration is calculated using standard deviation and coefficient of variation (CV) and the maximum allowable coefficient of variation is 10% CV, whereas day-to-day variation is examined by comparing the slope and intercept of calibration curves. The GSP is the blood galactose concentration obtained 60 seconds after stopping the 30-second injection.

8. Statistical Analysis

All data are represented in mean±standard deviation (SD) and the results are calculated using ANOVA to determine the significance. Statistical Package of the Social Science program (Version 13, SPSS Inc.) is used for calculations followed by post hoc test to examine the least significant difference for multiple comparisons so as to confirm the significant differences between groups and the average difference between groups was significant p<0.05.

Results

1. Results of Biochemical Analysis

At the time of completion the study, the weight and relative liver weight of the test animals were measured and no significant difference was found when compared with the animals in the normal control group. The results of blood biochemical analysis are shown in Table 1. Except for the activity of plasma AST and ALT in the APAP hepatotoxicity group was significantly higher than control group (the plasma AST level of the control and APAP group was 202±34 IU/L and 499±112 IU/L, respectively, $p<0.005$; the plasma ALT level of the control and APAP group was 56±14 IU/L and 368±71 IU/L, respectively, $p<0.005$), indicating liver damage has occurred in the APAP hepatotoxicity group. Except the results of the dicalcium phosphate group are not as expected, said liver damage can be improved by combined use of the safe recipients such as mannitol, menthol, sucralose and the measured liver inflammatory indicators AST, ALT and GSP as well as the Total HAI-score assessment based on the histological tissue sections all showed significant decrease. The results are shown in FIG. 1 and among which the combination of mannitol and sucralose showed the best protection effect and the result is similar to the control group.

TABLE 1

Mice in the control group, APAP hepatotoxicity group, and liver protection groups including dicalcium phosphate, mannitol, menthol, sucralose were administered with a single dose by tube feeding and GSP, AST level, ALT level and the Total HAI-score obtained from histological tissue sections were measured. Calculations of the values are shown in mean ± SD.

| Liver function parameters | GSP (mg/L) | AST (IU/L) | ALT (IU/L) | Total HAI-score |
|---|---|---|---|---|
| 1. normal control (n = 6) | 289 ± 38 | 202 ± 34 | 56 ± 14 | 0.0 ± 0.0 |
| 2. APAP hepatotoxicity group (n = 6) | 848 ± 123 | 499 ± 112 | 368 ± 71 | 4.9 ± 1.8 |
| 3. dicalcium phosphate (1.67 mg/kg) group (n = 6) | 444 ± 60*** | 315 ± 42* | 196 ± 65* | 3.1 ± 1.1* |
| 4. mannitol (1.67 mg/kg) group (n = 6) | 253 ± 29*** | 201 ± 30*** | 79 ± 34*** | 0.8 ± 0.3*** |
| 5. menthol (1.67 mg/kg) group (n = 6) | 289 ± 20*** | 187 ± 21*** | 109 ± 23*** | 11 ± 1.2** |
| 6. sucralose (1.67 mg/kg) group (n = 6) | 218 ± 31*** | 199 ± 24*** | 83 ± 23*** | 0.6 ± 0.4*** |
| 7. mannitol + sucralose (1.67 + 1.67 mg/kg) group (n = 6) | 236 ± 33*** | 198 ± 37*** | 59 ± 13*** | 0.5 ± 0.4*** |
| 8. mannitol + sucralose (0.83 + 0.83 mg/kg) group (n = 4) | 244 ± 19*** | 190 ± 23*** | 65 ± 19*** | 0.7 ± 0.5*** |
| 9. mannitol + sucralose (0.42 + 0.42 mg/kg) group (n = 4) | 281 ± 58*** | 187 ± 41*** | 96 ± 14*** | 1.4 ± 1.7* |
| 10. mannitol + sucralose(0.17 + 0.17 mg/kg) group (n = 4) | 371 ± 49*** | 298 ± 49* | 101 ± 24*** | 2.1 ± 1.2* |

2. Histopathology

Figure 2:
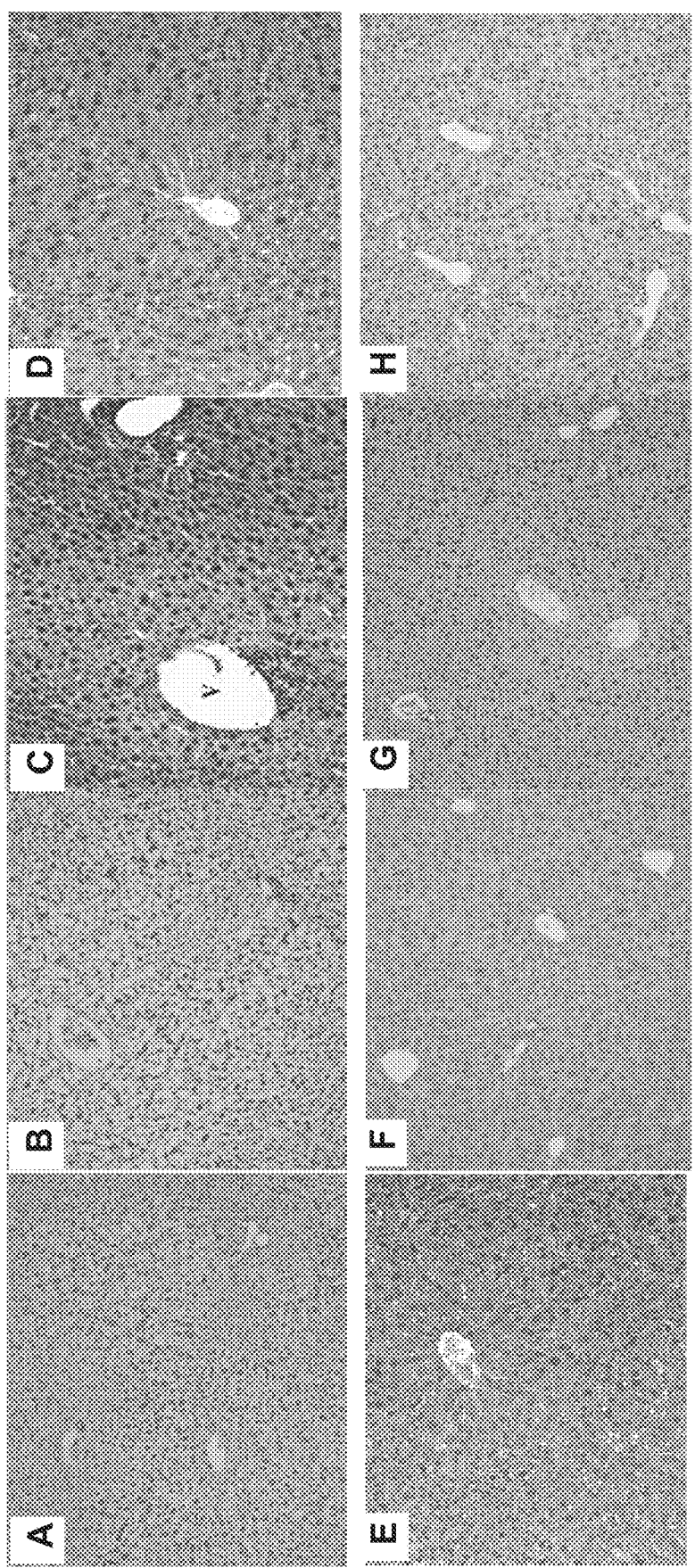
FIG. 2 shows tissue sections of rat liver from (A) normal control group, (B) APAP hepatotoxicity group, (C) dicalcium phosphate, (D) mannitol, (E) menthol, (F) sucralose, (G) mannitol+sucralose (1.67+1.67 mg/kg) and (H) mannitol+sucralose (0.83+0.83 mg/kg) liver protection group, tissue sections of rat liver after oral administration of a single dose of the compound (A) liver tissue morphology of normal control group, (B) the hepatocytes around the central vein (V) are broken and infiltrated with inflammatory cells and necrosis and vacuolization are present. When compared with the APAP hepatotoxicity groups, all hepatocytes of the rats in the liver protection groups are more intact around the central vein and have a apparent nucleus with less vacuolization (D, E, F, G and H) except for the dicalcium phosphate group and among which (F) and (G) are most similar to the liver tissue sections of normal rats (H&E stain, 200×).

The improved results are also reflected in the corresponding liver tissues. Rats fed with a single oral dose of 1000 mg/kg APAP successfully produced hepatotoxicity in vivo. The liver tissue sections from the rats in the APAP hepatotoxicity group showed that hepatocytes surrounding the central vein are broken with visible vacuolization and reduced number of nucleuses, some hepatocytes even showed the signs of necrosis and liver damage is more severe when compared with the hepatocytes from rats in the normal control group (as shown in FIG. 2B). On the contrary, liver structure of rats in the control group are normal, the hepatocytes are intact and arranged in order with no vacuolization (as shown in FIG. 2A). As for the liver sections from the liver protection groups such as mannitol, menthol and sucralose, the hepatocytes are relatively intact with visible nucleus and less vacuolization (as shown in FIGS. 2C, D, F, G and H), indicating the liver tissues from the mannitol, menthol and sucralose protection groups are similar to the liver tissues from the normal control group and among which mannitol and sucralose provide the best protection and said protection is positively correlated with dose, the higher the dose the better the protection.

3. Measurement of Residual Liver Function

As shown in FIG. 1, the GSP values of the control and APAP hepatotoxicity group shows significant differences (the GSP of control and hepatotoxicity group was 289±38 mg/L and 848±123 mg/L, respectively, $p<0.005$). In addition, the GSP values of the protection group dicalcium phosphate, mannitol, menthol and is sucralose were 444±60 mg/L, 253±29 mg/L, 289±20 mg/L and 218±31 mg/L, respectively and the differences between the GSP values of the protection groups and the hepatotoxicity group were significant when compared the APAP hepatotoxicity group ($p<0.005$). The GSP values increased significantly in the rats with hepatotoxicity after a single administration of APAP; however, combination use of APAP with excipients like mannitol, menthol and sucralose in the liver protection group can help against such change.

EXAMPLE 2

Screening of the Cytochrome P450 2E1 (CYP2E1) inhibitors-rat liver microsomes and human liver microsomes.

Materials and Methods
1. Materials

This example is preparation of microsomes from rat and human liver for in vitro screening of CYP2E1 inhibitors. A total of 55 safe and edible excipients are included in the screening for cytochrome P450 2E1 (CYP2E1) inhibitors. Effective rat or human hepatic CYP2E1 inhibitors were screened and the principle for screening the CYP2E1 inhibitors is based on the reaction of microsomal CYP2E1 prepared from the liver of different origin and its specific substrate Chlorzoxazone (CZX). After addition of the test sample, the amount of CYP2E1 metabolite standard 6-OH—CZX (6-Hydroxy-Chlorzoxazone) is used for calculation of the CYP 2E1 inhibition ratio of the test sample by using the amount of 6-OH—CZX of the control group as the baseline.

All test samples were dissolved in 10% methanol or distilled water and CYP 2E1 inhibition ratios were measured by adding excipients at different concentrations (66 uM, 33 uM, 16.5 uM; 0.167%, 0.08%, 0.042%, w/v). The results are shown in Table 2.

The reagents required for screening of the cytochrome CYP2E1 inhibitors from rat or human liver microsomes are as follows:
(1) CYP2E1: 100 mM potassium phosphate (pH 7.4) contains 10 mg/mL P450 protein concentration.
(2) Control Protein: 10 mg/mL P450 Protein was dissolved in 100 mM Potassium Phosphate (pH 7.4).
(3) Buffer Solution: 0.5 M Potassium Phosphate (pH 7.4).
(4) Stop Solution: ice-acetonitrile.
(5) Cofactors: contain 100 mM NADP+ and 10 mM Glucose 6-Phosphate.
(6) Glucose 6-Phosphate Dehydrogenase: 2000 units/ml was dissolved in sterile water.
(7) Chlorzoxazone: the substrate 16 mM Chlorzoxazone was dissolved in 10% methanol.
(8) DDTC (Diethyldithiocarbamic acid): CYP2E1 selective inhibitors (positive control group), 20 mM DDTC was dissolved in 10% methanol.
(9) NADPH-regenerating System: in 3.42 m, add 530 uL Cofactors, 40 uL G6PDH (Glucose 6-Phosphate Dehydrogenase Solution) and 100 uL Control Protein.

2. Screening of Cytochrome P450 2E1 (CYP2E1) Inhibitors

The procedures of screening for cytochrome P450 2E1 (CYP2E1) inhibitors from rat or human liver microsomes are as follows:
(1) In a water bath at 4° C., 0.1M phosphate buffered saline (pH 7.4) containing 0.5 mg/mL rat or human liver microsomes and 5 mM MgCl$_2$ were incubated for 15 minutes.
(2) add P450 2E1 substrate drug, 16 mM Chlorzoxazone, and the screened compound to the experimental groups and methanol:sterile water=1:1 and DDTC was added to the control groups and positive control group, respectively.
(3) Add cofactors 1 mM NADP+, 10 mM G6P and 2 IU G6PD in the is last. Transfer to and pre-incubate the reaction mixture in a water bath at 37° C. for 1 minute. The reaction time for testing activity is 30 minutes.
(4) After the reaction is completed, add 500 μL acetonitrile to stop the reaction. Incubate the sample for 1 minute and add internal standard (5 ug/mL 4-hydroxytobutamide). Collect 20 uL of the supernatant after centrifugation and diluted 10 fold using methanol:sterile water and take 5 uL of the resuspended solution and inject into the LC/MS/MS for analysis.
(5) Analysis of the results: convert the detected signal values obtained from LC/MS/MS into the amount (pmol) of CYP2E1 metabolite standard 6-Hydroxy-Chlorzoxazone using the control group as the baseline, i.e. the CYP 2E1 inhibition ratio of the control group is 0%, and calculate the CYP 2E1 inhibition ratio of the positive control group using the follow formula:

$$\text{CYP2E1 inhibition rate (\%)} = \left[1 - \frac{\text{Experimental Group 6-OH-CZX amount}}{\text{Control Group 6-OH-CZX amount}}\right] \times 100\%$$

Results
1. Positive Control Group

CYP 2E1 inhibition ratios of the positive control group (DDTC) are shown in Table 2. From Table 2, CYP 2E1 inhibition can reach 89.2% when the concentration of DDTC is at 100 μM.

2. CYP 2E1 Inhibition Ratios of the Experimental Groups

CYP 2E1 inhibition ratios of the excipients in the rat liver microsomes are shown in Table 2. From the results, excipients at different concentrations (66 μM, 33 μM, 16.5 μM; 0.167%, 0.08%, 0.042%, w/v) have different effects on P450 2E1 inhibition and among which 0.167% Brij 58 showed the best inhibition effect (100.0±0.00%).

TABLE 2

The inhibition ratios of CYP 2E1 inhibitors from in-vitro screening of rat liver microsomes

| Excipient | CYP 2E1 inhibition ratio (%) Test concentration | | |
|---|---|---|---|
| | 66 μM | 33 μM | 16.5 μM |
| Control group | 0 | | |
| Positive control group (DDTC) | (100 μM) 89.2 ± 2.2 | (50 μM) 50.4 ± 1.1 | (10 μM) 8.6 ± 1.1 |
| Brij 58 | 100.0 ± 0.0 (0.167%) | 98.6 ± 0.2 (0.084%) | 96.5 ± 0.3 (0.042%) |
| Brij 76 | 100.0 ± 0.0 (0.167%) | 98.5 ± 0.1 (0.084%) | 97.5 ± 0.3 (0.042%) |
| Tween 20 | 95.9 ± 0.4 (0.167%) | 92.5 ± 0.7 (0.084%) | 80.6 ± 1.9 (0.042%) |
| Tween 80 | 85.1 ± 0.4 (0.167%) | 79.4 ± 1.4 (0.084%) | 68.2 ± 1.3 (0.042%) |
| Microcrystalline cellulose | 78.7 ± 2.8 (0.025%) | 75.0 ± 5.2 (0.013%) | 73.9 ± 1.8 (0.006%) |
| Tween 40 | 78.1 ± 1.4 (0.167%) | 71.5 ± 0.5 (0.084%) | 54.0 ± 3.2 (0.042%) |
| Dicalcium phosphate dihydrate | 76.7 ± 0.8 | 62.0 ± 2.6 | 55.0 ± 4.6 |
| Saccharin | 67.4 ± 3.9 | 59.6 ± 3.3 | 35.3 ± 2.0 |
| Brij 35 | 67.2 ± 1.4 (0.025%) | 59.3 ± 2.5 (0.013%) | 45.9 ± 2.6 (0.006%) |
| Mannitol | 60.6 ± 3.3 | 51.0 ± 2.7 | 40.9 ± 2.8 |
| Cremophor RH40 | 57.4 ± 3.2 | 49.4 ± 2.9 | 48.0 ± 2.1 |
| Sucralose | 54.0 ± 4.2 | 46.8 ± 0.8 | 41.1 ± 2.7 |
| PEG 400 | 52.5 ± 4.6 (0.167%) | 43.4 ± 3.0 (0.084%) | 35.1 ± 2.2 (0.042%) |
| Crospovidone | 48.7 ± 0.4 | 43.2 ± 3.6 | 41.1 ± 2.7 |
| PEG 4000 | 48.1 ± 2.4 (0.167%) | 39.4 ± 1.8 (0.084%) | 32.7 ± 0.8 (0.042%) |
| Sodium starch glycolate | 41.2 ± 4.9 (0.167%) | 37.6 ± 2.5 (0.084%) | 34.1 ± 0.8 (0.042%) |
| S100 | 39.7 ± 4.9 | 33.5 ± 4.0 | 12.7 ± 1.9 |
| Eudragit S100 | 38.8 ± 2.4 (0.167%) | 35.9 ± 2.8 (0.084%) | 10.7 ± 4.0 (0.042%) |
| Croscarmellose sodium | 38.8 ± 2.4 (0.167%) | 35.9 ± 2.8 (0.084%) | 10.7 ± 4.0 (0.024%) |
| Pluronic F68 | 37.3 ± 3.0 (0.167%) | 18.9 ± 1.4 (0.084%) | 14.9 ± 0.9 (0.024%) |

TABLE 2-continued

The inhibition ratios of CYP 2E1 inhibitors from in-vitro screening of rat liver microsomes

| Excipient | CYP 2E1 inhibition ratio (%) Test concentration | | |
|---|---|---|---|
| | 66 μM | 33 μM | 16.5 μM |
| Menthol | 36.4 ± 0.3 | 15.3 ± 7.9 | 7.2 ± 2.9 |
| Low-substituted hydroxypropyl cellulose | 36.2 ± 6.0 (0.025%) | 33.8 ± 1.4 (0.013%) | 28.7 ± 2.2 (0.006%) |
| Pregelatinized starch | 33.6 ± 2.0 (0.167%) | 26.2 ± 2.8 (0.084%) | 14.0 ± 2.5 (0.024%) |
| Dextrates, NF hydrate | 32.9 ± 2.0 (0.167%) | 27.0 ± 3.0 (0.084%) | 13.2 ± 0.6 (0.024%) |
| Citric acid | 27.6 ± 3.6 | 12.4 ± 2.2 | 7.5 ± 2.3 |
| Cremophor EL | 25.2 ± 2.7 (0.167%) | 12.9 ± 2.2 (0.084%) | 5.9 ± 0.3 (0.024%) |
| Aerosil 200 | 23.8 ± 2.4 (0.167%) | 22.8 ± 1.7 (0.084%) | 4.7 ± 1.2 (0.024%) |
| Myrj 52 | 20.5 ± 0.3 (0.167%) | 18.5 ± 0.6 (0.084%) | 17.5 ± 1.5 (0.024%) |
| PEG 8000 | 19.2 ± 2.0 (0.167%) | 15.1 ± 0.6 (0.084%) | 9.9 ± 0.3 (0.024%) |
| Sorbic acid | 19.0 ± 5.6 | 13.2 ± 4.4 | 12.1 ± 5.7 |
| Lemon oil | 18.2 ± 3.7 (0.167%) | 13.9 ± 2.9 (0.084%) | 9.7 ± 3.8 (0.024%) |
| Hydroxypropyl cellulose | 18.0 ± 2.2 (0.167%) | 12.7 ± 1.9 (0.084%) | 6.7 ± 0.7 (0.024%) |
| Span 60 | 17.1 ± 0.8 (0.167%) | 15.2 ± 2.1 (0.084%) | 15.1 ± 1.4 (0.024%) |
| Sorbitol | 16.1 ± 0.7 (0.167%) | 5.6 ± 0.5 (0.084%) | 6.4 ± 0.5 (0.024%) |
| Sodium benzoate | 15.8 ± 0.9 | 7.8 ± 4.1 | 7.1 ± 2.0 |
| Acesulfame potassium | 14.5 ± 1.9 | 7.1 ± 2.3 | 3.9 ± 2.7 |
| Hydroxypropyl methylcellulose | 13.9 ± 2.2 (0.167%) | 13.6 ± 2.6 (0.084%) | 6.7 ± 0.7 (0.024%) |
| Hydroxy ethylmethylcellulose | 11.6 ± 0.9 (0.167%) | 13.2 ± 0.6 (0.084%) | 5.6 ± 0.5 (0.024%) |
| Methylcellulose | 10.3 ± 1.7 (0.167%) | 5.2 ± 0.3 (0.084%) | 5.0 ± 1.1 (0.024%) |
| Span 80 | 9.4 ± 0.6 (0.167%) | 8.5 ± 1.3 (0.084%) | 10.6 ± 1.9 (0.024%) |
| Sodium cyclamate | 9.1 ± 2.6 | 5.7 ± 4.7 | 9.4 ± 2.7 |
| Lactose monohydrate | 8.7 ± 3.8 | 7.8 ± 2.2 | 3.9 ± 2.3 |
| Maltodextrin | 8.5 ± 2.8 (0.167%) | 5.9 ± 2.1 (0.084%) | 9.7 ± 5.6 (0.024%) |
| Glyceryl behenate | 8.2 ± 2.0 | 3.1 ± 2.5 | 3.1 ± 0.2 |
| Oxide red | 8.5 ± 5.1 | 10.7 ± 4.1 | 10.3 ± 2.1 |
| Glycerin monostearate | 6.9 ± 1.8 (0.167%) | 7.4 ± 2.9 (0.084%) | 8.3 ± 5.7 (0.024%) |
| Copovidone K28 | 6.1 ± 0.7 (0.167%) | 4.5 ± 0.5 (0.084%) | 4.3 ± 0.2 (0.024%) |
| Starch acetate | 5.3 ± 0.7 (0.167%) | 4.9 ± 1.2 (0.084%) | 5.5 ± 1.2 (0.024%) |
| Magnesium stearate | 5.0 ± 1.6 | 3.0 ± 0.7 | 2.0 ± 1.0 |
| Sodium lauryl sulfate | 4.8 ± 1.2 | 6.4 ± 0.9 | 4.6 ± 1.1 |
| Providone K30 | 3.2 ± 0.2 | 2.2 ± 0.1 | 4.7 ± 1.0 |
| Benzyl alcohol | −10.3 ± 6.3 (0.167%) | 6.7 ± 1.0 (0.084%) | 8.2 ± 2.0 (0.024%) |
| Methylparaben | −21.5 ± 2.0 | −14.6 ± 4.1 | 4.6 ± 3.2 |
| Propylparaben | −27.3 ± 3.7 | −17.2 ± 2.4 | −4.1 ± 1.2 |
| Solutol H15 | −35.5 ± 4.3 (0.167%) | −21.0 ± 4.8 (0.084%) | −9.3 ± 0.8 (0.042%) |
| Butylated hydroxylanisol | −85.5 ± 3.9 | −47.1 ± 5.3 | −16.8 ± 2.5 |

The CYP 2E1 inhibition ratios of th excipients detected in the human liver microsomes are shown in Table 3. From the results, excipients at different concentrations (66 μM, 33 μM, 16.5 μM; 0.167%, 0.08%, 0.042%, w/v) have different effects on P450 2E1 inhibition and among which 0.167% Brij 58 showed the best inhibition effect (91.2±1.3%).

TABLE 3

The inhibition ratios of CYP 2E1 inhibitors from in-vitro screening of human liver microsomes

| Excipient | CYP 2E1 inhibition ratio (%) Test concentration | | |
|---|---|---|---|
| | 66 μM | 33 μM | 16.5 μM |
| Control group | 0 | | |
| Positive control group (DDTC) | (100 μM) 89.6 ± 0.9 | (50 μM) 49.8 ± 2.9 | (10 μM) 7.3 ± 1.0 |
| Brij 58 | 91.2 ± 1.3 (0.167%) | 80.5 ± 1.1 (0.084%) | 62.6 ± 2.1 (0.042%) |
| Brij 76 | 86.2 ± 1.3 (0.167%) | 75.7 ± 1.6 (0.084%) | 69.0 ± 3.8 (0.042%) |
| Saccharin | 78.5 ± 2.1 | 51.2 ± 0.9 | 29.4 ± 2.7 |
| Brij 35 | 77.3 ± 1.0 (0.025%) | 73.0 ± 1.7 (0.013%) | 42.4 ± 1.8 (0.006%) |
| Tween 20 | 75.4 ± 3.6 (0.167%) | 70.4 ± 0.9 (0.084%) | 55.4 ± 1.9 (0.042%) |
| PEG 400 | 64.2 ± 1.5 (0.167%) | 54.8 ± 3.5 (0.084%) | 26.4 ± 1.8 (0.042%) |
| Microcrystalline cellulose | 60.2 ± 4.1 (0.025%) | 54.4 ± 3.8 (0.013%) | 48.8 ± 0.2 (0.006%) |
| Dicalcium phosphate dihydrat | 60.1 ± 0.3 | 56.8 ± 2.2 | 31.2 ± 2.9 |
| Sucralose | 55.8 ± 2.0 | 45.8 ± 4.0 | 37.1 ± 2.8 |
| Mannitol | 54.5 ± 4.2 | 51.2 ± 2.1 | 44.8 ± 1.8 |
| Cremophor RH40 | 50.4 ± 1.1 | 43.2 ± 3.1 | 30.2 ± 2.8 |
| Sodium starch glycolate | 49.1 ± 2.9 (0.167%) | 31.4 ± 5.2 (0.084%) | 38.9 ± 1.3 (0.042%) |
| PEG 2000 | 47.5 ± 1.5 (0.167%) | 41.4 ± 1.6 (0.084%) | 22.3 ± 1.9 (0.042%) |
| PEG 4000 | 47.1 ± 0.9 (0.167%) | 23.9 ± 2.9 (0.084%) | 8.7 ± 1.8 (0.042%) |
| Tween 40 | 46.3 ± 3.1 (0.167%) | 33.4 ± 2.7 (0.084%) | 16.9 ± 1.2 (0.042%) |
| Crospovidone | 44.1 ± 0.9 (0.167%) | 40.3 ± 3.3 (0.084%) | 35.6 ± 1.8 (0.042%) |
| Tween 80 | 39.1 ± 2.4 (0.167%) | 40.6 ± 3.8 (0.084%) | 29.0 ± 1.7 (0.042%) |
| S100 | 38.3 ± 0.1 (0.167%) | 35.6 ± 2.4 (0.084%) | 23.2 ± 3.5 (0.042%) |
| Eudragit S100 | | | |
| Croscarmellose sodium | 35.4 ± 4.8 (0.025%) | 30.3 ± 5.4 (0.013%) | 8.1 ± 2.3 (0.006%) |
| Pluronic F68 | 31.5 ± 1.6 (0.025%) | 17.4 ± 4.2 (0.013%) | 7.9 ± 0.8 (0.006%) |
| Menthol | 30.8 ± 0.3 | 20.8 ± 2.1 | 10.5 ± 0.4 |
| Low-substituted hydroxypropyl cellulose | 22.1 ± 3.7 (0.025%) | 20.3 ± 1.8 (0.013%) | 17.5 ± 2.9 (0.006%) |
| PEG 8000 | 21.1 ± 4.4 (0.167%) | 14.2 ± 3.6 (0.084%) | 9.4 ± 0.2 (0.024%) |
| Citric acid | 20.5 ± 1.8 | 15.5 ± 1.5 | 9.9 ± 3.1 |
| Cremophor EL | 19.2 ± 0.5 (0.167%) | 15.1 ± 2.2 (0.084%) | 8.1 ± 0.6 (0.024%) |
| Dextrates, NF hydrate | 19.2 ± 1.1 (0.167%) | 14.4 ± 3.2 (0.084%) | 12.9 ± 0.6 (0.024%) |
| Pregelatinized starch | 18.3 ± 2.4 (0.167%) | 12.8 ± 0.8 (0.084%) | 9.9 ± 0.1 (0.024%) |
| Myrj 52 | 18.1 ± 2.6 (0.167%) | 15.7 ± 2.8 (0.084%) | 14.6 ± 1.7 (0.024%) |
| Span 60 | 17.4 ± 0.9 (0.167%) | 13.9 ± 0.7 (0.084%) | 12.4 ± 2.3 (0.024%) |
| Aerosil 200 | 15.7 ± 3.4 (0.167%) | 17.8 ± 2.1 (0.084%) | 7.8 ± 0.4 (0.024%) |
| Sorbic acid | 14.8 ± 0.1 | 10.9 ± 2.7 | 8.4 ± 1.6 |
| Span 80 | 10.1 ± 2.1 (0.167%) | 5.7 ± 4.7 (0.084%) | 9.4 ± 2.7 (0.024%) |
| Lemon oil | 7.8 ± 0.3 (0.167%) | 9.8 ± 0.4 (0.084%) | 8.8 ± 1.1 (0.024%) |

The effective dose range of the excipients at different concentrations (66 μM, 33 μM, 16.5 μM) for the new hepatotoxicity-free pharmaceutical composition for improving hepatotoxicity induced by Acetaminophen (APAP) drugs is: 0.17-5.5 g polyethylene glycol sorbitan monolaurate (Tween 20), 100~1000 mg microcrystalline cellulose, 10-250 mg dicalcium phosphate dihydrate, 100-1000 mg Brij 35, 10-40 mg saccharin, 10-250 mg mannitol, 0.17-5.5 g cremophor RH40, 10-250 mg sucralose, 0.17-5.5 g crospovidone, 0.17-5.5 g sodium starch glycolate, 0.17-5.5 g Eudragit S100, 0.17-5.5 g croscarmellose sodium, 1.4-5.5 g Pluronic F68, 8-34 mg menthol, 0.19-0.82 g low-substituted hydroxypropyl cellulos, 1.7-5.5 g pregelatinized starch, 0.17-5.5 g dextrates NF hydrated, 10-42 mg citric acid, 1.7-5.5 g cremophor EL, 0.17-5.5 g Aerosil 200, 1.4-5.5 g Myrj 52, 6-24 mg sorbic acid, 0.17-5.5 g lemon oil, 0.17-5.5 g hydroxypropyl cellulose, 0.17-5.5 g sorbitol, 1.4-5.5 g acesulfame potassium, 0.17-5.5 g hydroxypropyl methylcellulose, 6-24 mg lactose monohydrate, 0.17-5.5 g maltodextrin, 0.17-5.5 g Brij 58, 0.17-5.5 g Brij 76, 0.17-5.5 g Tween 80, 1.4-5.5 g Tween 40, 1.4-5.5 g PEG 400, 1.4-5.5 g PEG 4000, 1.4-5.5 g PEG 8000, 1.4-5.5 g Span 60, 2.9-11.9 mg sodium benzoate, 0.17-5.5 g hydroxy ethylmethylcellulose, 0.17-5.5 g methylcellulose, 1.4-5.5 g Span 80, 3.3-13.2 mg sodium cyclamate, 17.4-69.9 mg glyceryl behenate, 11.3-45.2 mg oxide red, 1.4-5.5 g glycerin monostearate, 0.17-5.5 g Copovidone K28, 0.17-5.5 g starch acetate, 9.7-39.0 mg magnesium stearate, 4.7-19.0 mg is sodium lauryl sulfate, 0.18-0.73 mg Providone K30 and 1.4-5.5 g PEG 2000.

The new hepatotoxicity-free pharmaceutical composition provided in this invention significantly reduced hepatotoxicity caused by acetaminophen in terms of biochemical analysis (ALT and AST levels), pathological analysis and residual liver function (GSP levels) when compared with single administration of acetaminophen.

The foregoing examples and embodiments are merely better examples of the present invention; therefore, it should be understood that they are only for illustration purpose and shall not limit the scope of the present invention. Any variations or modifications made according to the claims of the present invention are remain within the scope of the present invention. For example, the types, used concentrations and ratios of acetaminophen, cytochrome P450 2E1 inhibitors and selection of the cytochrome P450 2E1 inhibitors, shall remain within the scope of the present invention.

In conclusion, the invention not only provides a novel application of acetaminophen but also reduces hepatotoxicity caused by acetaminophen by combination use of acetaminophen with common and safe excipients.

What is claimed is:

1. A pharmaceutical composition consisting of acetaminophen, mannitol and sucralose, wherein mannitol and sucralose are in an amount effective in reducing, eradicating, or preventing hepatotoxicity caused by acetaminophen.

2. The pharmaceutical composition of claim 1, wherein acetaminophen, mannitol and sucralose are used separately, simultaneously or sequentially.

3. The pharmaceutical composition of claim 1, which is in the form of gel, solution, capsule, torches, or tablets, in a pharmaceutically acceptable dosage form.

4. The pharmaceutical composition of claim 1, wherein the acetaminophen, mannitol and sucralose are included in pharmaceutical kits, pharmaceutical packs or patient packs and acceptable container.

* * * * *